(12) United States Patent
Seitz et al.

(10) Patent No.: US 10,520,751 B2
(45) Date of Patent: Dec. 31, 2019

(54) APPARATUS AND METHOD FOR DETERMINING OPTICAL PARAMETERS

(71) Applicant: Rodenstock GmbH, Munich (DE)

(72) Inventors: Peter Seitz, Munich (DE); Markus Tiemann, Munich (DE); Gregor Esser, Munich (DE); Werner Mueller, Oetisheim (DE)

(73) Assignee: Rodenstock GmbH, Munich (DE)

( * ) Notice: Subject to any disclaimer, the term of this patent is extended or adjusted under 35 U.S.C. 154(b) by 192 days.

(21) Appl. No.: 15/521,476

(22) PCT Filed: Sep. 15, 2015

(86) PCT No.: PCT/EP2015/001844
§ 371 (c)(1),
(2) Date: Apr. 24, 2017

(87) PCT Pub. No.: WO2016/062363
PCT Pub. Date: Apr. 28, 2016

(65) Prior Publication Data
US 2017/0336654 A1 Nov. 23, 2017

(30) Foreign Application Priority Data
Oct. 23, 2014 (DE) .......................... 10 2014 015 671

(51) Int. Cl.
G02C 7/02 (2006.01)
A61B 3/08 (2006.01)
G02C 13/00 (2006.01)

(52) U.S. Cl.
CPC ................ *G02C 7/025* (2013.01); *A61B 3/08* (2013.01); *G02C 7/027* (2013.01); *G02C 7/028* (2013.01); *G02C 13/003* (2013.01)

(58) Field of Classification Search
CPC ........ G02C 7/02; G02C 13/00; G02C 13/005; G02C 13/003; G02C 7/025; G02C 7/027;
(Continued)

(56) References Cited

U.S. PATENT DOCUMENTS

| 7,740,355 B2* | 6/2010 | Sessner | ................ G02C 13/005 351/204 |
| 2013/0286351 A1* | 10/2013 | Shimizu | ................ A61B 3/107 351/212 |

FOREIGN PATENT DOCUMENTS

| DE | 102005003699 A1 | 7/2006 |
| DE | 102010007922 A1 | 8/2011 |

(Continued)

OTHER PUBLICATIONS

European Patent Office, PCT International Search Report, 5 pages, dated Nov. 27, 2015.
(Continued)

*Primary Examiner* — James R Greece
(74) *Attorney, Agent, or Firm* — Schiff Hardin LLP

(57) ABSTRACT

An apparatus for determining optical parameters of a user with spectacles arranged in the use position on the head of the user includes at least one projection device designed and arranged for marking a partial region of the head of the user and/or of the spectacles of the user with a light projection; at least one image recording device designed and arranged for generating image data at least from the marked partial region of the head of the user and/or of the spectacles of the user; and a data processing device with a user data determining device, which is designed to determine user data from the marked partial region of the head and/or of the spectacles on the basis of the generated image data, wherein the user data comprise spatial information in the three-dimensional space of points of the partial region of the head and/or of the spectacles, and a parameter determining (Continued)

Figure 1:
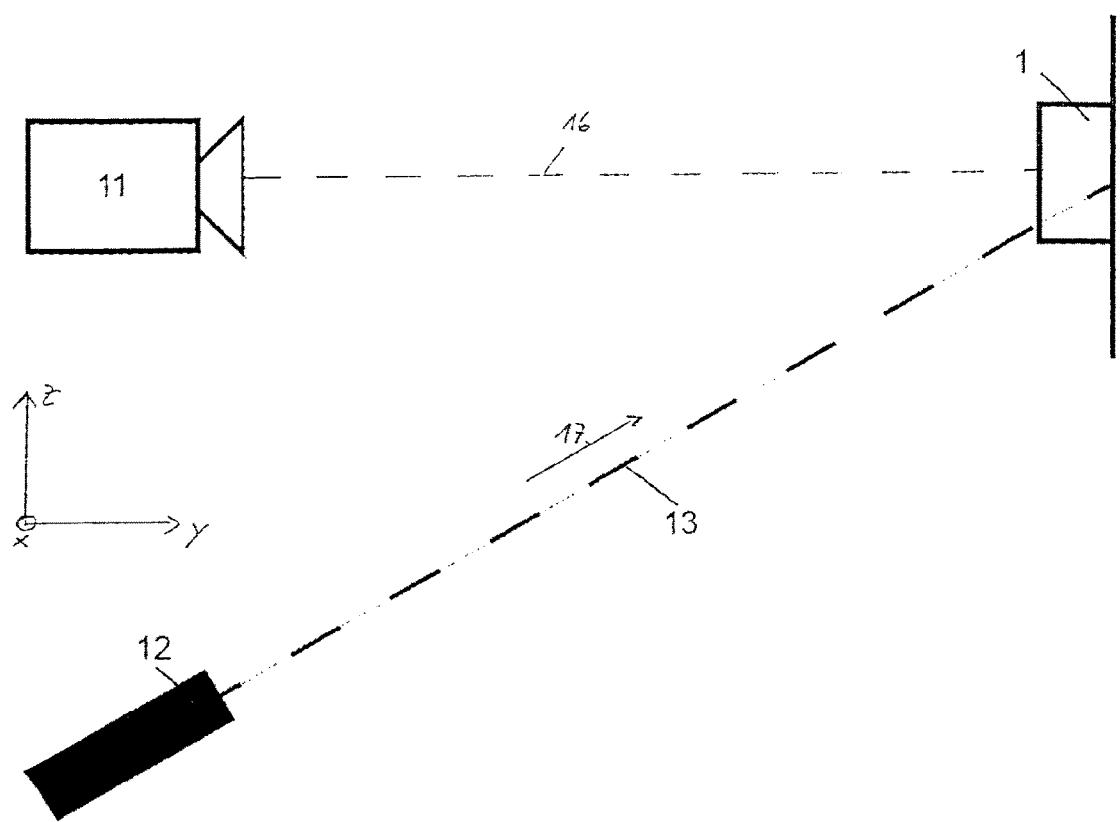

device, which is designed to determine optical parameters of the user on the basis of the user data.

20 Claims, 2 Drawing Sheets

(58) Field of Classification Search
CPC ........... G02C 7/028; A61B 3/08; A61B 3/111; A61B 3/112; A61B 3/113
USPC .................................. 351/159.76, 205, 206
See application file for complete search history.

(56) References Cited

FOREIGN PATENT DOCUMENTS

| | | |
|---|---|---|
| JP | H8-275920 A | 10/1996 |
| JP | 2005-106491 A | 4/2005 |
| JP | 2008-536149 A | 9/2008 |
| JP | 2012-239566 A | 12/2012 |

OTHER PUBLICATIONS

Von Bernhard Muff, XP000098546, "Die Brille aus Dem Computer", 1155 Technische Rundschau, vol. 80, No. 45, pgs. 52-53, Nov. 4, 1988.
Office Action dated Jan. 22, 2019 for Japanese Patent Application No. 2017-522049.

\* cited by examiner

APPARATUS AND METHOD FOR DETERMINING OPTICAL PARAMETERS

The present invention relates to an apparatus for determining optical parameters of a user; a method for determining optical parameters of a user; and a computer program product for implementing the method.

Via the introduction of individually optimized spectacle lenses, it is possible to address the needs of persons with visual defects, and to provide spectacle lenses with individually optimized visual regions, for example. Individually adapted spectacle lenses enable an optimal correction of optical visual defects of a user of the spectacle lenses. An individual calculation and adaptation of spectacle lenses is also possible for sports glasses, which are characterized by large deflections, face form angles and forward inclination angles.

In order to completely exploit the optical advantages of individual spectacle lenses, in particular of individually adapted varifocal lenses, it is necessary to calculate and manufacture these spectacle lenses with knowledge of the use position of the user, and for them to be worn according to the use position used for calculation and manufacturing. The use position is dependent on a plurality of parameters, for example on the pupillary distance of the user, the face form angle, the forward inclination of the spectacle lens, the spectacle frame, the corneal vertex distance of the system of spectacles and eye, and the fitting height of the spectacle lenses. These and additional parameters which may be used or are necessary to describe the use position are contained in relevant standards, for example DIN EN ISO 1366, DIN 58 208, DIN EN ISO 8624 and DIN 5340. It is also necessary that the spectacle lenses are arranged or centered in a spectacle frame corresponding to the optical parameters which were used for manufacturing such that, in the use position, the spectacle lenses are actually worn corresponding to the optical parameters.

To determine the position of a spectacle lens in front of the eye, multiple parameters must be determined. On the one hand, the information required for fitting and insertion into the frame may thereby be obtained; on the other hand, optimizations may therefore be made in the spectacle lens itself in order to adapt it to the wear position when in the usage position.

For example, to determine such parameters an apparatus with two image recording devices is known from DE 10 2005 003 699 A1, which apparatus takes a respective image of a user with spectacles from different recording directions, from which images said apparatus calculates three-dimensional user data, for example.

Other apparatuses operate with two-dimensional calculation methods that determine the desired parameters using multiple images. In addition to this, there are possibilities for manual determination, for example a pupilometer and a pupillary distance ruler.

In all of these measurement methods, there is a dependency on the measuring person and the implementation of the measurement. For example, the individual corneal vertex distance cannot be determined given the determination of the pupillary distance using a two-dimensional image, whereby a systematic deviation of the pupillary distance results that is dependent on test subject and frame.

Given use of a stereoscopic camera system to determine the optical parameters of a user in three-dimensional space, a correspondence problem occurs. The correspondence problem relates to an identification of points corresponding to one another in two images acquired from different perspectives. Only after points corresponding to one another in both images have been determined can a 3D reconstruction of the image points take place.

In practice, the corresponding points are determined via a manual evaluation of the images. This manual evaluation requires a significant time expenditure and, due to the user dependency, is a potential error source for the 3D reconstruction.

The invention is based on the object of providing an improved possibility of determining optical parameters of a user.

This object is achieved via the subject matters of the independent claims.

A first aspect relates to an apparatus for determining optical parameters of a user with a spectacles arranged on the head of the user, in a use position. The apparatus has at least one projection device which is designed and arranged to mark a partial region of the head of the user and/or of the spectacles of the user with a light projection. The apparatus furthermore has at least one image recording device which is designed and arranged to generate image data of at least one marked partial region of the head of the user and/or of the spectacles of the user. The image data may contain additional regions of the head-with-spectacles system. In addition to this, the apparatus has a data processing device having a user data determination device which is designed to determine user data of the marked partial region of the head and/or of the spectacles using the generated image data, wherein the user data include spatial information, in three-dimensional space, of points of the marked partial region of the head and/or of the spectacles. The data processing device furthermore has and [sic] a parameter determination device which is designed to determine optical parameters of the user using the user data.

The projection device generates the light projection. The projection device may be designed as a radiator that generates electromagnetic radiation. For example, the projection device may be designed as an LED or as a laser. The apparatus has at least one projection device, but may additionally have one or more further projection devices that expose an expanded partial region of the head of the user and/or of the spectacles of the user.

The partial region of the head of the user and/or of the spectacles of the user that is thereby exposed (thus marked) relates to a partial region of the "head-with-spectacles" system, thus of the head of the user and of the spectacles of the user arranged thereon in the use position. The use position is defined in the standards cited above, for example. Either a partial region of the head, a partial region of the spectacles, or preferably a partial region that has both parts of the head and parts of the spectacles may be marked with the light projection. Marked points in the partial region of the head may, for example, be one or both pupils, especially the center points of the pupils, as well as the root of the nose of the user insofar as this is not covered by the spectacles frame. Points of the marked partial region of the spectacles may in particular be points on the spectacles frame, for example temporally and/or nasally arranged inner and/or outer frame boundary points, as well as inner and/or outer frame boundary points arranged above and/or below the pupils. Multiple points of the partial region may be marked with the light projection.

The marking thereby preferably takes place with a light wavelength that may be detected quickly and with certainty in the image data, for example automatically via a computer-controlled evaluation.

For example, a digital camera may be used as an image recording device. The image recording device may comprise a digital camera and at least one optical deflection element or a deflection mirror, wherein the image data of the partial region are recorded and/or generated with the camera by means of the deflection mirror or deflection element.

The image recording device generates image data, which may take place via the recording of an image. The image data may thus represent digital data of a recording. The recording generated in such a manner thereby includes at least the partial region of the head and/or of the spectacles of the user that is marked by the light projection. The image data preferably include a recording of both eyes of the user, in particular of both pupils of the user, as well as the frame of the spectacles of the user. The marked partial region relates at least to individual points in this recording, and thus to at least individual points in these image data.

The apparatus may have a stereoscopic camera system, thus for example two image recording devices, that generate image data of the marked partial region from two different perspectives. Alternatively, the apparatus may have only one image recording device capable of swiveling, which image recording device generates image data of the marked partial region from two different perspectives.

The image data include at least the marked partial region of the head-with-spectacles system, but may include additional parts of the head and/or of the spectacles.

The data processing device may be designed as a computer and/or have a microprocessor. The user data determination device and the parameter determination device may operate independently of one another. The data processing device may be designed such that the user data determination device and the parameter determination device are operated by means of a common microprocessor. In other words, the data processing device is designed such that at least one microprocessor executes both the task(s) of the user data determination device and of the parameter determination device.

The image recording device may be designed and arranged such that at least one pupil of the user and a pupillary [sic] frame edge and/or a spectacles lens edge is mapped in the generated image data, wherein the at least one pupil of the user is defined by the spectacles frame edge and/or the spectacles lens edge in the generated image data.

The user data determination device generates user data. The user data include spatial information for a few points of the marked partial region. The user data are generated from the image data that include the marking via the light projection. For this, the image recording device is designed such that it can detect the light wavelength of the light projection. The image recording device is thus designed to be sensitive to the light wavelength range of the light projection. The user data may contain spatial information of individual points of the marked partial region in three-dimensional space, and/or enable a complete 3D reconstruction of the recording. A 3D reconstruction may take place mathematically, for example from two recordings by means of epipolar geometry. The user data may include spatial information for at least one of the following points:

an intersection point of a horizontal plane in the reference system of the user with the spectacles lens edges and/or the spectacles frame edges of the spectacles, wherein the horizontal plane of the user intersects both pupils of the user and travels parallel to a predetermined zero sight line of the user;

intersection point of a vertical plane in the reference system of the user with the spectacles lens edges and/or the spectacles frame edges of the spectacles, wherein the vertical plane of the user travels orthogonal to the horizontal plane of the user and parallel to the predetermined zero sight line of the user, and intersects a pupil of the user;

at least one center point of a pupil;

boundaries of at least one spectacles lens of the user according to a dimensioning in the boxing system;

spectacles center point of the spectacles frame of the spectacles.

What is to be understood by a dimensioning in the boxing system in the sense of this invention is the measurement system as it is described in relevant standards, for example in DIN EN ISO 8624 and/or DIN EN ISO 1366 DIN [sic] and/or DIN 58208 and/or DIN 5340. With regard to the boxing system and additionally used conventional terms and parameters, refer also to the book, "Die Optik des Auges and der Sehhilfen" ["The Optics of the Eye and of Visual Aids"] by Dr. Roland Enders, 1995 Optische Fachveröffentlichung GmbH, Heidelberg, as well as to the book "Optik and Technik der Brille" ["Optics and Engineering of Spectacles"] by Heinz Diepes and Ralf Blendowski, 2002 Verlag Optische Fachveroffentlichungen GmbH, Heidelberg. For the terminology definitions, the standards as well as the cited book [sic] inasmuch represent an integral disclosure component of the present application.

The boundaries according to a dimensioning in the boxing system include, for example, frame points for one eye or both eyes which are situated furthest outward or inward and/or above or below. These frame points are conventionally determined using tangents to the spectacles frame or regions of the spectacles frame that are associated with the respective eyes (see for example DIN 58 208; Illustration 3).

In the sense of this invention, the zero viewing direction is a view direction straight ahead given parallel fixed lines. In other words, it is a view direction which is defined by a position of the eye relative to the head of the user, wherein the eyes view a fixed object that is located at eye level and is arranged at an infinitely distant point. For example, the image recording device may be used as a fixed object. Since the real fixed object cannot be arranged at an infinite distance, in practice the viewing direction may be corrected from the distance of the eyes from the fixed object, with the assistance of an eye model, such that this corresponds to the zero viewing direction. In the sense of this invention, the zero viewing direction is consequently determined only by the position of the eyes relative to the head of the user. If the head of the user is located in a normal upright position, the zero viewing direction essentially corresponds to the horizontal direction in the reference system of the Earth. However, the zero viewing direction may be tilted relative to the horizontal direction in the reference system of the Earth, for example in the event that the user inclines his head forward or to the side without additional movement of the eyes. Analogously, a plane which is essentially parallel to the horizontal plane in the reference system of the Earth is spanned by the zero viewing direction of both eyes. The plane which is spanned by the two zero viewing directions of the two eyes may likewise be inclined relative to the horizontal plane in the reference system of the Earth, for example in the event that the user inclines his head forward or to the side.

The horizontal plane of the user may correspond to a first plane. The vertical plane of the user may correspond to a second plane which is orthogonal to the first plane. For example, the horizontal plane in the reference system of the user may be arranged parallel to a horizontal plane in the reference system of the Earth, and merely travel through the center point of a pupil. This is especially the case in the event that both eyes of the user are arranged at a different height (in the reference system of the Earth).

The parameter determination direction determines the sought optical parameters of the user from the user data. The optical parameters of the user may include at least one of the following values:
pupillary distance;
monocular pupillary spacing;
corneal vertex distance according to requirements of reference point and/or of eye's center of rotation;
monocular centering point spacing;
centering point coordinates;
disc spacing;
decentering of the centering point;
disc height and width;
disc center distance;
forward inclination of the spectacles lens;
face form angle;
fitting height.

The optical parameters furthermore preferably include a center of rotation of an eye and/or parameters using which a dynamic visual response of a user may be determined, for example convergence of an eye position and/or gaze deflection.

The pupillary distance essentially corresponds to the spacing of the pupil centers.

The optical parameters include especially preferred physiological and anatomical parameters of a spectacles wearer, frame-specific properties, as well as features of a spectacles-eye system of the user which, for example, is described in DIN 58208. The features of the spectacles-eye system of the user may, for example, be used to calculate spectacle lenses and for precise centering of spectacle lenses, [sic] centering data are determined exactly according to the cited standards relative to a disc or frame plane. The disc plane is hereby the plane through a horizontal and vertical (in the reference system of the Earth) center line in the right or left boxing system in the spectacles frame. The frame plane is the plane through center lines of the boxing systems establishing the right and left disc plane of the spectacles frame, which center lines are vertical relative to one another.

Via the light projection of the projection device, points of the partial region are marked so that an identification of specific positions in the image data is at least simplified. An automated or semi-automated identification of specific positions in the image data may especially be enabled by the marking. For example, points corresponding to one another may be identified in recordings of a stereoscopic camera system. For example, the correspondence problem that is relevant to a 3D reconstruction may thereby be solved. In that these same points (thus points corresponding to one another) are marked by the same marking (namely by the light projection) in both recordings, corresponding points may be identified simply and quickly. The data processing device may be designed either to detect and further use automatically determined marked points in the image data or to propose selected points to an operator (an optician, for example) who may confirm or reject these simply and quickly.

The apparatus thus simplifies the solving of the correspondence problem and enables an at least partially automated and/or computer-controlled identification of individual points in the image data. The danger of a possibly incorrect 3D reconstruction by the operator is thereby reduced.

Furthermore, the apparatus enables a simple determination of the optical parameters, especially without physical markings on the frame of the spectacles and/or on the user.

In one embodiment, the projection device is designed and arranged so that specific individual points on the head and/or on the spectacles of the user are marked by the light projection in the image data. The projection device is thereby designed such that the light projection may be specifically directed at predetermined points of the head-with-spectacles system so that these may be specifically marked. The partial region may have multiple such individual points that may be simply identified due to the marking in the image data, especially in a computer-controlled or computer-assisted manner.

In a development of this embodiment, the projection device is designed and arranged so that at least one of the following user points is specifically marked in the image data:
a center point of a pupil,
an outer temporal frame point,
an inner nasal frame point,
an inner frame point above the pupils and/or
an inner frame point below the pupils.

The terms "above" and "below" thereby relate to the reference system of the user, wherein "above" essentially means vertically above and "below" essentially means vertically below. The term "vertical" hereby relates to the reference system of the user. The terms "nasal" and "temporal" relate to points on the frame that are essentially horizontally distanced from the pupils. Optical parameters of the user that may be important to the optician can be especially advantageously determined from the user points indicated above, especially from all ten of the cited user points (the respective five cited user points for each eye). Advantageous user points in the partial region of the head and/or of the spectacles are thus preferably already marked with the light projection, which user points are converted by the user data determination device into user data with three-dimensional spatial information. The marked points may contain some user points, or may already contain all points (inclusive of the user points), about which spatial information is determined in three-dimensional space.

Given rimless frames, corresponding spectacle edge points may thereby be marked as an alternative to the cited frame points.

According to one embodiment, the projection device is designed and arranged so that the light projection in the image data at least partially has the form of at least one line, at least one line intersection and/or at least one point. Thin markings—for example a line—enable an especially simple identification of points in the image data, for example as an intersection point of the line with the frame of the spectacles, the pupil center point, an inner and/or outer frame edge, a spectacles edge etc. The points may be marked with a line, with a line intersection, and/or by means of a point of the projection device. For example, the light projection may have a projection plane emanating from an optical center point of the projection device, which projection plane essentially marks the partial region in the form of a line. This line adapts to the optical conditions of the user and/or of the spectacles frame and therefore may exhibit slight curvatures and/or interruptions in the image data, for example given a jump from the face of the user to a frame edge. The terms "line", "line intersection" and/or "point" are thus hereby not to be understood exactly in a mathematical sense, but rather insofar as that the points marked by the light projection lie essentially on a line or essentially at a point. Individual points in the image data can be identified especially simply via such an embodiment of the projection device.

The light projection may be designed such that it has a maximum extent of 2 mm, preferably of at most 1 mm, in at least one dimension in the head-with-spectacles system. This maximum extent may relate to a maximum line width and/or a maximum point diameter in the head-with-spectacles system, for example.

According to one embodiment, the projection device is calibrated relative to the image recording device, and the user data determination device uses information about this calibration to determine the user data. The calibration hereby includes information about the position and the projection direction of the projection device relative to the position and relative to the direction vector of the optical axis of the image recording device. The optical center point of the projection device may, for example, be arranged at a well-defined distance from the optical center point of the image recording device. Furthermore, the direction vector of the projection device and the direction vector of the optical axis of the image recording device are known beforehand in the reference system of the apparatus. This information about direction and position that is known beforehand is designated as calibration. The calibration of the projection device relative to the image recording device may be fixed. Alternatively, one of the two devices may also be variably adjustable, wherein in this embodiment the position relative to one another—thus the calibration of the two devices—may be measured and determined and subsequently may be stored in the user data determination device.

The user data determination device uses information about the calibration to determine the user data. For example, if the light projection has a line and is arranged parallel to the lines of the image data, the distance of the apparatus from the user may be determined by means of triangulation, depending on the line height of the projected line in the image data. If information about the calibration is stored in the user data determination device, the apparatus may determine the necessary optical parameters of the user with a single recording, thus a single set of image data. The user data may hereby be determined as three-dimensional spatial information in particular in a reference system of the calibrated apparatus.

According to one embodiment, the projection device has an adjustable projection direction. The projection device may thus be designed so as to be movable together with at least parts of the apparatus, such that the projection direction may be set. For example, if the light projection has the form of a line, this line may be placed through the two pupil center points of the user in the recording of the image data. In addition to the projection direction, the position of the projection device may also be adjustable. This enables a targeted marking of specifically selected points in the marked partial region of the head of the user and/or of the spectacles of the user, which points are especially advantageous for the determination of the optical parameters (for example some or all of the aforementioned user points). The light projection may additionally or alternatively be adjusted so that at least one part of the light projection travels essentially vertically (in the reference system of the user) through at least one pupil of the user, such that the light projection vertically intersects the spectacles frame.

According to one embodiment, the light projection that has been provided by the projection device includes at least one projection plane that at least partially projects a line onto the exposed partial region of the head and/or of the spectacles of the user. Intersection points of the line with the frame of the spectacles, a spectacles edge and/or the pupil center point may hereby mark individual points in the image data.

In a development of this embodiment, the projection device is calibrated relative to the image recording device so that the optical axis of the image recording device and the projection plane intersect at a previously known intersection angle. Within the scope of this application, the optical axis of the image recording device is not necessarily the optical axis of a camera itself, but rather the optical axis that strikes the head-with-spectacles system of the user, for example after deflection at one or more mirrors. The projection plane similarly designates that plane of the light projection that strikes the head-with-spectacles system of the user. The projection plane and/or the projection direction of the light projection may also be modified by one or more optical structural elements such as mirrors, prisms, beam expanders etc. after it leaves the light source (for example LED or laser). Information about this calibration enables a calculation of user data by the user data determination device.

In a development of this embodiment, the intersection angle known in advance is at least 10° and at most 70°. Intersection angles in this range that are known in advance are particularly well-suited as a predetermined calibration of the apparatus. The intersection angle known in advance is preferably at least 20°, especially preferably at least 30°. Furthermore, the intersection angle known in advance is preferably at most 60°. In an especially preferred embodiment, the intersection angle known in advance is from 40° to 50°.

In one embodiment, the light projection provided by the projection device includes at least two projection planes that intersect at a predetermined angle. The apparatus is designed and arranged so that the intersection line of the two projection planes is contained as an intersection point in the image data. For example, the intersection point of the two projection planes may be placed at a pupil center point in the image data. For example, the intersection point of the two projection planes may be placed at a pupil center point in the image data. The intersection angle of the two projection planes is preferably at least 90°. If the projection direction is adjustable, one projection plane is placed essentially vertically and one is placed essentially horizontally in the reference system of the user, for example, wherein the intersection point is arranged at a pupil center point.

According to one embodiment, the user data determination device is designed and arranged so that the user data determination device determines the user data from image data that are generated with a single recording of the image recording device. The determination of the data from a single recording that includes points marked by the light projection enables an especially fast determination of the optical parameters. In this embodiment, the apparatus requires only a single image recording device that may, by means of a single recording, record all information that the data processing device requires to determine the optical parameters. The user data determination device may hereby use information about a calibration of the apparatus.

In an embodiment as an alternative to this, the user data determination device is designed and arranged so that it determines the user data from two sets of image data from two different recording positions. The apparatus may hereby either have at least two image recording devices that generate essentially simultaneous recordings from two recording positions or an image recording device that can be swiveled and acquires two recordings from different recording positions. The two sets of image data hereby respectively contain the marking by means of the light projection, such that the correspondence problem in the image data may simply be solved with the aid of the marking.

In a development of this embodiment, the user data determination device is designed and arranged so that it uses the marking by the light projection to identify corresponding image points in the two sets of image data. In this embodiment, the marking thus serves for a simplified solution of the correspondence problem in the 3D reconstruction.

According to one embodiment, the projection device provides the light projection in an invisible wavelength. In order to not irritate the user, radiation of a wavelength that is imperceptible to the human eye is preferably used. Therefore, in this embodiment the light projection may be adjusted without disturbing the user so that it travels directly through the pupils of the user. For example, the light projection may be in the infrared wavelength range, whereby the user is not blinded. There is a plurality of standard components as mass-produced articles for image recording and for exposure in the spectral range above the visible spectrum (for example in infrared). The corresponding apparatus may thereby be realized cost-effectively. The invisible wavelength is registered by the image recording device. This is thus sensitive in the invisible wavelength range used by the light projection.

In principle, the light projection may also be realized in other spectral ranges, especially in the visible spectral range or in the UV range.

In one embodiment, the light projection may include different wavelengths that enable an additional differentiation and marking of individual points of the head-with-spectacles system of the user.

In one embodiment, the apparatus has a preview output device that displays on which partial region of the head and/or of the spectacles of the user the light projection is aligned. In particular, in the embodiment with the invisible wavelength an adjustment of the projection device is enabled by the preview output device, such that said projection device marks the desired partial region. The preview output device may, for example, be designed as a display that indicates the light projection in a wavelength that is visible at the preview output device. The light projection is thus only indicated at the preview output device, without blinding the user.

According to one embodiment, the apparatus is designed as a portable, mobile apparatus. Portable and mobile hereby means that the apparatus weighs at most 10 kg, preferably at most 5 kg, especially preferably at most 2 kg. In this embodiment, the apparatus can be handled so that it may be carried by an operator, in particular to house calls or to events. The apparatus may thereby be carried and operated in the hand of an operator. For mobile use, for example, the objective of the image recording device may be used as a fixed object for the user, who gazes at the objective in the zero viewing direction.

According to one embodiment, the apparatus has a data output device which is designed to output at least one part of the defined optical parameters of the user. The data output device may be designed as a monitor and/or display. The optical parameters are displayed at the data output device and may be read out there. The data output device may also provide the optical parameters as digital data that may be read out from another apparatus.

A second aspect relates to a method to determine optical parameters of a user with spectacles arranged in the use position on the head of the user, wherein:

a partial region of the head of the user and/or of the spectacles of the user is marked with a light projection, image data of at least the marked partial region of the head of the user and/or of the spectacles of the user are generated, user data of the marked partial region of the head and/or of the spectacles are determined using the generated image data, wherein the user data include spatial information of points of the partial region of the head and/or of the spectacles in three-dimensional space, and optical parameters of the user are determined using the user data.

The method is especially suited to determining the optical parameters using the apparatus according to the first aspect.

According to one embodiment, the user data are determined under consideration of a calibration of the light projection relative to the positioning and alignment if an image recording device to generate the image data. Information about the calibration hereby enter into the calculation of the user data, for example in order to determine the user data in three-dimensional space with the aid of calculations in epipolar geometry.

In a development of this embodiment, a distance between the position of the image recording device and the position of the user is estimated from the image data by means of triangulation, under consideration of the calibration. This distance serves as an important variable in order to be able to determine the additional user data.

According to one embodiment, in the generation of the image data the light projection is adjusted so that a projection plane of the light projection travels through both pupils of the user. The projection plane may additionally intersect the frame of the spectacles and/or the spectacles edge. This adjustment of the light projection enables an especially simple determination of the optical parameters.

A third aspect relates to a computer program product including program parts which, when loaded in a computer, are designed to implement a method according to the second aspect.

Figure 2:
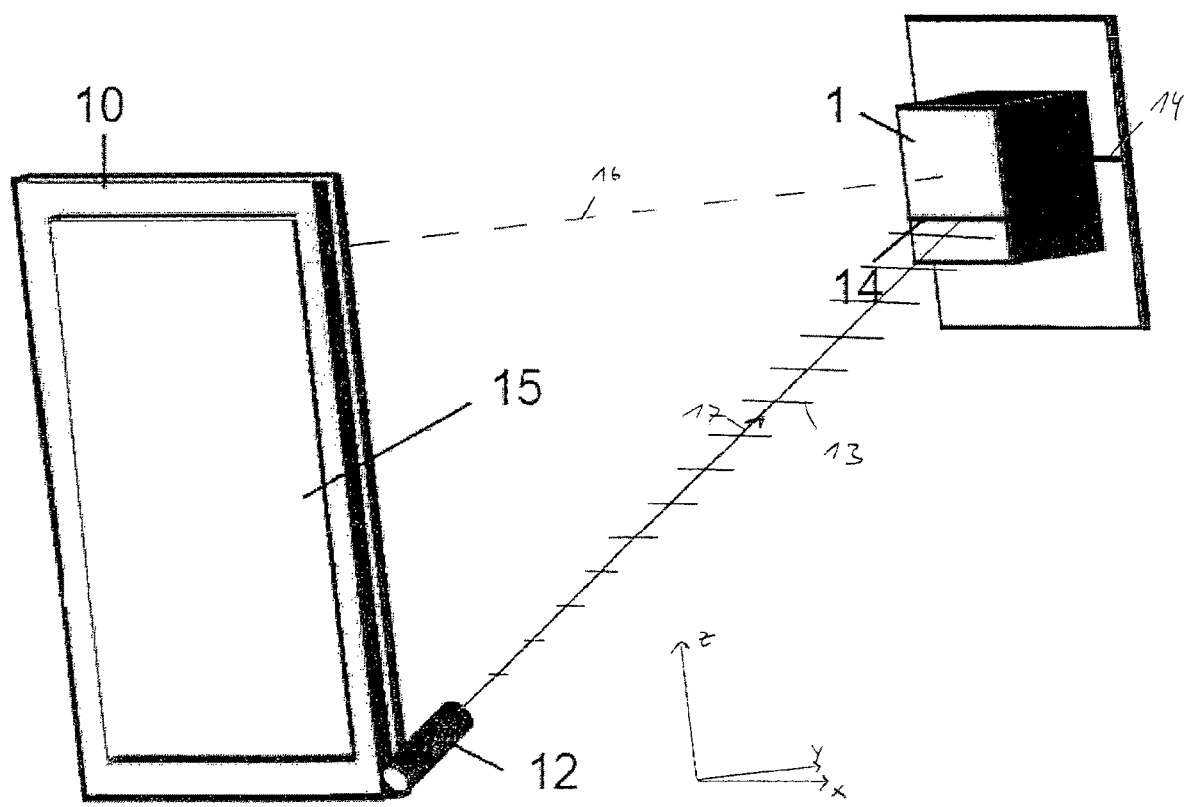
Figure 3:
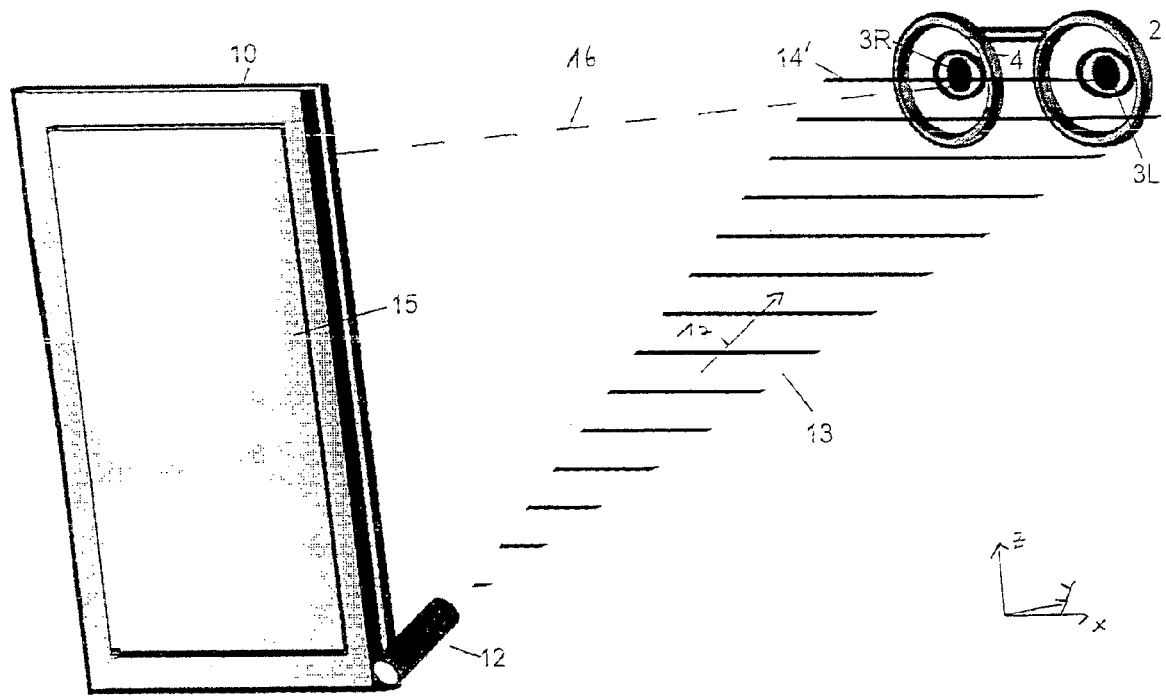
Figure 4:
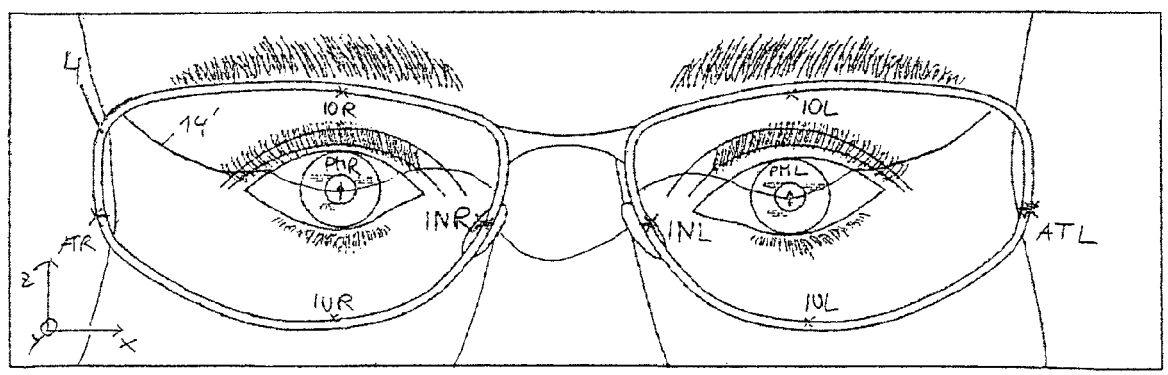

The invention is explained in detail in the following using aspects of the invention presented by Figures. Shown are:

FIG. 1 schematic presentation of an arrangement of components of an apparatus for determining optical parameters in a lateral view;

FIG. 2 perspective, schematic presentation of an apparatus for determining optical parameters, FIG. 3 perspective, schematic presentation of an apparatus for determining optical parameters with user and spectacles, and FIG. 4 a schematic presentation of a recording of a user with spectacles, with marking.

FIG. 1 shows a schematic presentation of components of an apparatus for determining optical parameters, in a lateral view. An image recording device 11 and a projection device 12 are shown in FIG. 1 as components of the apparatus. The image recording device 11 may be designed as a camera, for example, in particular as a digital camera. The projection device 12 may be designed as a light source, in particular as a line light source.

Both the image recording device 11 and the projection device 12 are aligned on a subject 1 that serves merely to illustrate the measurement method and is essentially cuboid in shape.

The image recording device 11 and the projection device 12 are calibrated to one another. In the coordinate system drawn in FIG. 1, the image recording device 11 and the light projection device 12 have a separation known in advance in the Z-direction. Furthermore, information about the alignment of the image recording device 11 and the light projection device 12 belongs among the calibration. In the coordinate system of FIG. 1, the image recording device 11 is aligned so that the direction vector of the the [sic] optical axis 16 of the image recording device 11 essentially coincides with the Y-direction. The projection device 12 is aligned in a projection direction 17 that has both a Y-component and a Z-component but no X-component.

The direction vector of the optical axis 16 and the direction vector of the projection device 17 intersect at an angle known beforehand. The size of the angle and the separation of the image recording device 11 from the projection device 12 are components of the calibration of the apparatus. The separation of the image recording device 11 from the light projection device 12 serves as a triangulation basis with which the separation of the subject 1 from the image recording device 11 may be determined, a separation in the Y-direction in the shown exemplary embodiment.

The projection device 12 generates a light projection that is radiated in the projection direction 17 and marks a partial region of the subject 1. The components of the apparatus are arranged so that this marking is included in the image data acquired by the image recording device 11. In other words, the marking caused by the light projection is visible in the recording.

In Figures, the Z-direction is arranged essentially vertically in the reference system of the user; the Y-direction is arranged essentially horizontally from the image recording device 11 toward the user 1 or the subject 1, and the X-direction is arranged essentially horizontally through the two pupil center points of the user 2 and/or orthogonal to the optical axis 16 of the image recording device 11.

In a perspective, schematic presentation, FIG. 2 shows an apparatus 10 having the two components already shown in FIG. 1. The image recording device 11 is thereby covered by the back side of the apparatus 10, such that only its optical axis 16 is shown in FIG. 2. The projection device 12 projects a marking 14 in the form of a line on the subject 1. The marking line extends in the X-direction and therefore is not visible in FIG. 1. The projection device 12 emits light in a projection plane 13 along the projection direction 17 that appears as a line on the subject 1. The direction vector of the projection direction 17 thereby points from the projection device 12 toward the subject 1. The emitted light beam of the light projection has a certain width (for example at least 10 cm in the subject distance from the image recording device) but essentially no height. The shape of the light projection relative to the projection plane 13 thereby results. The direction vector of the projection direction 17 thereby lies in the projection plane 13. Furthermore, the projection plane 13 has an essentially horizontal component that is arranged orthogonal to the plane of the drawing shown in FIG. 1. The projection plane 13 is therefore shown from the side in FIG. 1 as a line in the projection direction 17.

The marking 14 generated by the projection device 12 essentially has the form of a solid line. In the recording recorded by the image recording device 11, a portion of the marking 14 appears further below (as viewed in the Z-direction), another portion appears further above (see FIG. 2). Portions of the subject 1 that are arranged closer to the image recording device 11 are intersected further below (in the negative Z-direction) by the light projection in the form of a line, and therefore are likewise arranged further below in the image recorded with the image recording device 11. As is visible in FIG. 2, the portion of the marking 14 that is projected onto the wall arranged behind the subject 1 is arranged further above in the Z-direction than that portion of the marking 14 that is projected onto the portion of the subject 1 protruding in the negative Y-direction.

The separation of the points of the marked partial region from the image recording device 11 and/or from the apparatus 10 can thus be determined in the image data in that the position of the marked points in the recording is determined, in particular the position on the Z-axis in the shown embodiment. Via the calibration of the apparatus 10, the separation (in the Y-direction) of the marked points on the subject 1 in the image data of the image recording device 11 relative to the subject 1 can thus be calculated by means of triangulation.

As shown in FIG. 2, the apparatus 10 has a display 15 that is arranged on the side of the apparatus 10 facing away from the subject 1. The display 15 may, for example, be designed as a monitor or display. The display 15 may, for example, be used as a data output device that displays the optical parameters determined by the apparatus 10.

In addition or as an alternative to this, the display 15 may be designed and provided to display a preview of the image data together with the marking 14 generated by the projection device 12. The display 15 thus generates a preview of the image to be recorded as serves as a preview output device. This is especially advantageous if the projection device 12 generates radiation in a non-visible wavelength, for example in infrared, which is not visible to a human user. To adjust and/or align the apparatus 10 relative to the subject 1, an operator (for example an optician) may see on the display 15 which partial region of the subject 1 the projection device 12 marks.

FIG. 3 shows the apparatus 10 known from FIG. 2 in a perspective, schematic presentation from a perspective similar to as in FIG. 2. In contrast to the subject 1 schematically depicted in FIG. 2, a user 2 with spectacles 4 is schematically arranged in FIG. 3. Given the recording of the image data, the projection direction 17 of the projection device 12, and especially the projection plane 13, are aligned so that the marking 14' that is thereby generated travels through the two pupil centers of the user 2. The marking 14' travels through the center of the right pupil 3R of the user 2 and the center of the left pupil 3L of the user 2. Furthermore, the marking 14' intersects the frame of the spectacles 4 at multiple nasal and temporal positions of the frame, especially at inner and outer nasal and temporal frame points of the spectacles 4. Spatial information regarding some of these points may preferably be determined as user points in order to particularly advantageously calculate the optical parameters.

FIG. 3 thereby shows the marking 13' only schematically. In the image data generated by the image recording device 11, the marking 14'—similar to the marking 14 schematically depicted in FIG. 2—appears as a line that is in particular interrupted upon transition from the frame to the head of the user, since the frame of the spectacles 4 is arranged closer to the image recording device 11 than the marked partial region of the head, for example the two pupils 3L and 3R of the user 2.

The separation of the marked points on the frame of the spectacles 4, as well as of the marked points on the head of the user 2, from the image recording device 11 may be calculated by means of triangulation from the different Z-positions of the marking 14' in the recording recorded by the image recording device 11. User data in three-dimensional space may thereby be calculated. User data may be calculated by means of a user data determination device that may access a microprocessor of the apparatus 10. Optical parameters of the user 2 may be determined from the user data by a parameter determination device.

The apparatus 10 uses an active exposure in order to determine the optical parameters, such as centering data and individual parameters of the user, in a design for video centering by means of a 3D reconstruction.

As an alternative to the apparatus shown in Figures, a stereo camera system may also be used that generates image data from two different perspectives, for example from the document DE 10 2005 003 699 A1. The active exposure provided via an additional projection device 12 may hereby be used to solve and/or to accelerate the solving of the correspondence problem, which results if points corresponding to one another must be identified in the recordings from two different perspectives.

The user 2 may use the image recording device 11 or another point of the apparatus 10 as a fixed object that he fixes given the recording of the image data. The distance of the fixed object that is used from the pupils of the user may subsequently be used for convergence correction. Alternatively, a point that can be determined relative to the user 2 may be used as a fixed point, for example the nasal root of the user in a mirror image, wherein the mirror image is provided by a mirror that is attached to the image recording device 11 at a position known in advance.

Embodiment with a Stereo Camera System

In a stereo camera system as mentioned above as an apparatus for determining optical parameters of the user, the marking may be used in order to localize points corresponding to one another in image data that are recorded simultaneously or with chronological offset. This may take place via automatic and/or manual image processing. The manual evaluation may thereby be reduced to the first set if epipolar lines of the marking projected as a line do not coincide in the two sets of image data. From a point selected in the first set of image data, the corresponding point in the second set of image data is established by the epipolar line and the intersection point with the projected marking. This intersection point may be determined via automatic image processing, for example.

The stereo camera system may also have only one image recording device that records two sets of image data from different viewing angles toward the user with chronological offset. In this instance, the calibration of the camera positions is not necessarily known in advance and may be determined from the recorded image data in a method step. For calibration, for example, the position of the pupils 3L and/or 3R relative to the frame of the spectacles may be used. Since the pupils and the frame are located at different distances from the two positions of the image recording device, a corresponding offset results depending on the observation direction.

In addition to the two pupils of the user, five characteristic points on the frame that are respectively selected in both sets of image data may be used for the determination of the orientation. If a moving point is predetermined as a fixed object, two other, invariant points on the user and/or the frame may be selected instead of the two pupils of the user. A 3D reconstruction of the points from the acquired image data may take place from these seven points in total via the 7-point algorithm known from epipolar geometry.

Embodiment with One Set of Image Data

In the embodiment of the apparatus as it is presented in Figures, the optical parameters are determined from a single recording (thus from a single set of image data). The image recording device 11 and the projection device 12 are hereby calibrated relative to one another and internal to the apparatus. A calculation of the user data in three dimensions is enabled from the marking 14 or 14' in the image data that is generated by the projection device 12. An alignment of the marking 14, 14' may thereby be set in which the marking generated as a line is arranged essentially orthogonal to the epipolar plane. A triangle may thereby be used as a triangulation basis object, wherein the triangulation basis is aligned essentially vertically (in the Z-direction in Figures).

Via a mechanical and/or automatic image processing of the image data and/or a manual selection of the two pupil center points, the pupil separation (for example) may be determined in three dimensions from the image data. Additional parameters may be determined from the marked points and the generated user data, for example the face form angle and the horizontal section of the topography of the eye, as well as approximately the corneal vertex distance, the disc length to the left, the disc length to the right etc. An evaluation of the image data of a single recording hereby takes place along the projected marking (along the line in the shown embodiment). The evaluation can thereby be implemented very quickly.

Additional optical parameters may be determined via an additional second projection of an additional second line, for example a vertical line (not shown in Figures). In contrast to the essentially horizontally aligned first marking 14 and 14', this essentially vertically aligned second marking that is generated by (for example) a second projection device can be calibrated by means of a second triangulation basis. For this, for example, a horizontal distance (in the X-direction in the shown embodiment) of the second projection device from the image recording device 11 may be known in advance. In any event, a direction vector of the second projection device relative to the optical axis 16 as well as a position of the second projection device relative to the image recording device 11 may be known in advance as additional information.

Via this additional, essentially vertical marking, additional optical parameters may be calculated, for example the forward inclination, the disc height, the corneal vertex distance etc.

This second marking may thereby be positioned so that it is arranged over a pupil, thus travels essentially vertically through the right or left pupil of the user.

In one embodiment, multiple—in particular two—such vertical markings are projected onto the head-with-spectacles system in the form of a line. In one exemplary embodiment, two vertical markings parallel to one another in the form of a line are used whose distance from one another corresponds essentially to the typical pupillary distance (meaning approximately 64 mm) at a predetermined measurement distance from the camera. Additional optical parameters may thereby be determined, and in fact separately from one another for each eye.

A triggering of the image recording device, thus a recording of the image data, may take place automatically. A detection, thus a recording of the image data, may hereby be executed during the positioning of the apparatus if suitable trigger conditions are satisfied and detected, for example automatically detected pupil positions.

In the apparatus 10 presented in Figures, the light projection generated by the projection device 12 has a projection direction 17 that generates an essentially horizontal marking 14' on a user 2. The marking generated by the projection device 12 is hereby preferably aligned parallel to the lines in the image data of the image recording device, in particular if this is designed as a digital camera. This enables a simple triangulation basis and distance determination of the marked image points in the image data.

The marking enables a simplified selection of individual points in the image data, especially at intersection points of the marking with the frame edge and/or with the pupil center points.

FIG. 4 shows a schematic presentation of a recording of the head system of a user with spectacles 4, which was recorded by the apparatus 10 that is shown in FIGS. 1-3. The image data recorded by the image recording device 11 may correspond to the recording schematically shown in FIG. 4.

The recording contains image data of both pupils of the user as well as of the frame of the spectacles 4. The recording was recorded by the apparatus 10 counter to the zero viewing direction of the user, and is designed as a two-dimensional recording. The image data contain the marking 14' generated by the light projection unit 12 by means of the projection plane 13. The marking 14' in the recording thereby essentially has the form of a line. In order to clarify the different height of the marking 14' (thus the different position on the Z-axis) in the image data, the variation of the projected line in the Z-axis direction in FIG. 4 is presented in an exaggerated form. In a real recording, the marking 14' would essentially have more the form of a line.

Upon triggering the recording, the projected marking 14' was aligned so that it travels through the two pupil center points PMR and PML of the user.

The curve of the marking 14' is described in the following from left to right through the recording shown in FIG. 4, thus essentially in the positive X-direction. The marking 14' there travels from the right outer temporal frame point ATR across the frame edge to the right inner temporal frame point (not separately marked). From this point, the marking 14' "jumps" in the positive Z-direction (thus upward) in the recording to a position to the right (in the negative X-direction) of the right eye of the user. From there, the marking 14' travels across the right pupil center point PMR in the direction of the nasal root. From there, the marking 14' "jumps" to the frame at a nasal position, more precisely at the right inner nasal frame point INR, to the right outer nasal frame point (not marked), and further across the nose of the user after an additional "jump".

From there, the marking 14' travels essentially with mirror symmetry across the left eye and frame half, in particular the left inner nasal frame point INL, the left pupil center point PML, up to the left outer temporal frame point ATL.

The image data of the recording shown in FIG. 4 contain pixel positions of each image point, for example. The X-, Y- and Z-coordinates of each marked point may be determined by means of triangulation from these X- and Z-pixel positions, using the calibration. For example, the Y-coordinate may thus be determined by means of triangulation and information via the calibration for the marked points, depending on the respective Z-pixel position of the marked point. The conversion of the real X- and Z-coordinate of the marked point from the X- and Z-pixel positions in the image data may be calculated depending on the Y-coordinate by means of a scaling factor. Spatial information in three-dimensional space may thus be determined for each marked point, especially for the six targeted marked points ATR, PMR, INR, INL, PML and ATL.

All of these six points ATR, PMR, INR, INL, PML and ATL are specifically marked in the image data by means of the marking line provided by the projection unit 12. As explained above, the optical parameters of pupillary distance, disc length to the left, disc length to the right, face form angle, the horizontal section of the topography of the eye, the approximate corneal vertex distance etc. may be calculated as explained above from the three-dimensional spatial information of these six selected points of the head-with-spectacles system.

With an additional second light projection, and thus second marking in the vertical direction, the points of the right inner frame point above the pupils IOR, once again the right pupil center point PMR, and right inner frame point above the pupil IUR may additionally be marked. These points are shown in FIG. 4, but without the corresponding second marking.

Under consideration of information about the calibration of this second light projection (for example in the horizontal direction), spatial information in three-dimensional space may be determined for each point marked by the second light projection, especially for the three specifically marked points IOR, PMR and IUR. With the three-dimensional spatial information of these additional points, the additional optical parameters of forward inclination, disc height, corneal vertex distance etc. may be calculated for the right eye.

Analogous to this, the additional the [sic] points of left inner frame point above the pupil IOL, again the left pupil center point PML, and left inner frame point below the pupil IUL may be marked with an additional third light projection parallel to the second light projection in the vertical direction. These points are shown in FIG. 4 without the corresponding third marking.

Under consideration of information about the calibration of this third light projection (for example in the horizontal direction), spatial information in three-dimensional space may be determined for each point marked by the third light projection, especially for the three specifically marked points IOL, PML and IUL. With the three-dimensional spatial information of these additional points, the additional optical parameters of forward inclination, disc height, corneal vertex distance etc. may be calculated for the left eye.

Upon triggering the recording, these optional second and third marking line are aligned so that a respective marking line travels vertically (parallel to the Z-axis) through a respective pupil center point PMR or PML of the user.

The calculation of two examples of optical parameters from the three-dimensional spatial information of the points cited above is described in the following:

The optical parameter "pupillary distance" may be calculated as a length between the points PMR and PML in three-dimensional space. A division of the pupillary distance into right pupillary distance and left pupillary distance may additionally take place as an additional optical parameter. For this, a pupil center plane may be defined that has the same distance from the points INL and INR, and thus is arranged between these two points. The intersection point of this pupil center plane with a connecting line of the two points PMR and PML provides a division of the optical parameter "pupillary distance" into the right pupillary distance (as a section of this intersection point to the PMR) and the left pupillary distance (as a section of this intersection point to the PML).

The optical parameter "face form angle" may be calculated in a horizontal projection from the angle between the straight lines that are provided by the sections ATR-INR and ATL-INL.

In general, more and/or other than the ten points explicitly cited above may be used for the calculation of the optical parameters. For the optical parameters "disc length" and "disc height", only an approximate calculation is possible with the cited ten points. For a precise calculation of these parameters, the boxing system stated above may be used that may be taken into account in the user data.

To determine the boxing system as a component of the user data, a selection of a boundary of the spectacles lens may be performed (for example by the user data determination device) via a rectangle in the image data. Boundary lines of the boundary can thereby be shifted only using predefined directions. An upper boundary line may thus be arranged as a horizontal line in the disc plane and be depicted accordingly as a projection in the image data. This upper boundary line may be shifted only along a vertical direction, for example. For an inner boundary line, only a horizontal shift may be analogously provided, wherein the inner boundary line is depicted as a vertical line in the disc plane. A determination of the three-dimensional spatial information of the vertices of the boxing system may take place via the already selected points at which three-dimensional spatial information is present, as well as via scaling factors linking these points.

REFERENCE LIST 1 subject
2 user
3R right pupil
3L left pupil
4 spectacles
10 apparatus
11 image recording device
12 projection device
13 projection plane
14 marking
14' marking
15 display
16 optical axis
17 projection direction
PMR right pupil center point
PML left pupil center point
ATR right outer temporal frame point
ATL left outer temporal frame point
INR right inner nasal frame point
INL left inner nasal frame point
IOR right inner frame point above the pupil
IOL left inner frame point above the pupil
IUR right inner frame point below the pupil
IUL left inner frame point below the pupil

The invention claimed is:

1. An apparatus for determining optical parameters of a user with spectacles arranged in a use position on the head of the user, comprising:
at least one projection device which is designed and arranged to mark a partial region of the head of the user and/or of the spectacles of the user with a light projection;
at least one image recording device which is designed and arranged to generate image data of at least the marked partial region of the head of the user and/or of the spectacles of the user; and
a data processing device, comprising:
a user data determination device which is designed to determine user data of the marked partial region of the head and/or of the spectacles using the generated image data,
wherein the user data include spatial information in three-dimensional space of points of the partial region of the head and/or of the spectacles; and
a parameter determination device which is designed to determine optical parameters of the user using the user data,
wherein the at least one projection device is designed and arranged such that so that predetermined individual points on the head and/or the spectacles of the user are marked in the image data by the light projection, the optical parameters of the user being determined using the predetermined individual points that are marked in the image data.

2. The apparatus according to claim 1, wherein the at least one projection device is designed and arranged so that, in the image data, the predetermined individual points on the head and/or the spectacles of the user include one or more of:
a pupil center point,
an outer temporal frame point,
an inner nasal frame point,
an inner frame point above the pupil; and
an inner frame point below the pupil.

3. The apparatus according to claim 1, wherein the at least one projection device is designed and arranged so that the light projection in the image data at least partially has the form of at least one line, at least one line intersection, and/or at least one point.

4. The apparatus according to claim 1, wherein the at least one projection device is calibrated relative to the at least one image recording device, and the user data determination device uses information about this calibration to determine the user data.

5. The apparatus according to claim 1, wherein the at least one projection device has an adjustable projection direction.

6. The apparatus according to claim 1, wherein the at least one projection device is calibrated relative to the at least one image recording device so that the optical axis of the at least one image recording device and the projection plane intersect at an intersection angle of at least 10° and at most 70°, which intersection angle is predetermined.

7. The apparatus according to claim 1, wherein the light projection provided by the at least one projection device contains at least two projection planes that intersect at a predetermined angle.

8. The apparatus according to claim 1, wherein the user data determination device is designed and arranged so that it determines the user data from image data that are generated with a single recording of the at least one image recording device.

9. The apparatus according to any claim 1, wherein the user data determination device is designed and arranged so that it determines the user data from two sets of image data from different recording positions, and uses the line through the light projection to identify corresponding image points in the two sets of image data.

10. The apparatus according to claim 1, wherein the at least one projection device provides the light projection in an invisible wavelength.

11. The apparatus according to claim 10, further comprising:
a preview output device that displays on which partial region of the head and/or of the spectacles of the user the invisible light projection is aligned.

12. The apparatus according to claim 1, wherein the apparatus is designed as a portable, mobile apparatus.

13. A method to determine optical parameters of a user with spectacles arranged in the use position on the head of the user, comprising:
marking a partial region of the head of the user and/or of the spectacles of the user with a light projection,
generating image data of at least the marked partial region of the head of the user and/or of the spectacles of the user, determining user data of the marked partial region of the head and/or of the spectacles using the generated image data, the user data including spatial information in three-dimensional space of points of the partial region of the head and/or of the spectacles; and determining optical parameters of the user using the user data, wherein generating the image data includes marking predetermined individual points on the head and/or the spectacles of the user being marked in the image data by the light projection, wherein the optical parameters of the user are determined using the predetermined individual points that are marked in the image data.

14. The method according to claim 13, wherein the user data are determined under consideration of a calibration of the light projection relative to the positioning and alignment of an image recording device to generate the image data.

15. The method according to claim 14, wherein a distance between the position of the image recording device and the position of the user is estimated from the image data by means of triangulation, taking into account the calibration.

16. The method according to claim 13, wherein the light projection is adjusted in the generation of the image data so that the projection plane of the light projection travels through both pupils of the user.

17. A non-transitory computer readable medium including instructions that, when executed by one or more processors, cause the one or more processors to determine optical parameters of a user with spectacles arranged in the use position on the head of the user by:

marking a partial region of the head of the user and/or of the spectacles of the user with a light projection;

generating image data of at least the marked partial region of the head of the user and/or of the spectacles of the user;

determining user data of the marked partial region of the head and/or of the spectacles using the generated image data, the user data including spatial information in three-dimensional space of points of the partial region of the head and/or of the spectacles; and determining optical parameters of the user using the user data, wherein generating the image data includes marking predetermined individual points on the head and/or the spectacles of the user being marked in the image data by the light projection, wherein the optical parameters of the user are determined using the predetermined individual points that are marked in the image data.

18. The apparatus according to claim 1, wherein the projection plane has a direction that is parallel to a line through two pupil center points of the user.

19. The apparatus according to claim 1, wherein the at least one projection device and the at least one image recording device are disposed apart from one another in a direction that is substantially orthogonal to the projection plane.

20. The apparatus according to claim 1, wherein the light projection emanating from the at least one projection device in accordance with a projection plane that results in the partial region being marked in the form of a line.

* * * * *